(12) United States Patent
Pryor et al.

(10) Patent No.: US 12,257,180 B2
(45) Date of Patent: Mar. 25, 2025

(54) HYPOTHERMIC TREATMENT SACK

(71) Applicant: North American Rescue, LLC, Greer, SC (US)

(72) Inventors: Micah Pryor, Taylors, SC (US); Ian Dunbar, Zavalla, TX (US)

(73) Assignee: NORTH AMERICAN RESCUE, LLC, Greer, SC (US)

( * ) Notice: Subject to any disclaimer, the term of this patent is extended or adjusted under 35 U.S.C. 154(b) by 178 days.

(21) Appl. No.: 17/531,680

(22) Filed: Nov. 19, 2021

(65) Prior Publication Data
US 2023/0157865 A1 May 25, 2023

(51) Int. Cl.
*A61F 7/00* (2006.01)

(52) U.S. Cl.
CPC .... *A61F 7/0097* (2013.01); *A61F 2007/0002* (2013.01); *A61F 2007/0018* (2013.01); *A61F 2007/0039* (2013.01)

(58) Field of Classification Search
CPC ...... A61F 2007/0002; A61F 2007/0018; A61F 2007/0039; A61F 2007/0238; A61F 2007/0249; A61F 7/0097; A61F 7/02; A61F 7/03; A61F 7/032
See application file for complete search history.

(56) References Cited

U.S. PATENT DOCUMENTS

| | | | | |
|---|---|---|---|---|
| 4,884,303 A * | 12/1989 | Scherer | ................... | A47G 9/086 5/413 R |
| 5,386,604 A * | 2/1995 | Ricketts | ................... | A61G 1/01 5/413 R |
| 5,405,370 A * | 4/1995 | Irani | ..................... | A61F 7/0097 607/104 |
| 6,319,864 B1 * | 11/2001 | Hannigan | ............... | B32B 27/12 442/268 |
| 2005/0188464 A1 * | 9/2005 | DuPree | ................ | A61G 10/005 5/625 |
| 2008/0021530 A1 * | 1/2008 | Castellani | ................. | A61F 7/03 607/108 |
| 2009/0117802 A1 * | 5/2009 | Press | ........................ | B32B 5/26 427/430.1 |
| 2016/0029723 A1 * | 2/2016 | Neff | ..................... | A41D 27/207 2/250 |

OTHER PUBLICATIONS

Wiggy's, "Victims Casualty Hypothermia Bag" https://www.wiggys.com/sleeping-bags/victims-casualty-hypothermia-bag/, retrieved on Oct. 9, 2023, 4 pages.

* cited by examiner

*Primary Examiner* — Tigist S Demie
(74) *Attorney, Agent, or Firm* — Dority & Manning, P.A.

(57) ABSTRACT

Hypothermic treatment sacks are provided. A hypothermic treatment sack includes a top sheet that defines a first outer perimeter. The hypothermic treatment sack further includes a bottom sheet that defines a second outer perimeter. The first outer perimeter of the top sheet is removably coupled to the second outer perimeter of the bottom sheet such that a patient receiving cavity is defined between the top sheet and the bottom sheet. The top sheet and the bottom sheet include a weather resistant external layer, a heat reflective interior layer, and an insulation layer. The insulation layer is disposed between the external layer and the heat reflective interior layer.

20 Claims, 4 Drawing Sheets

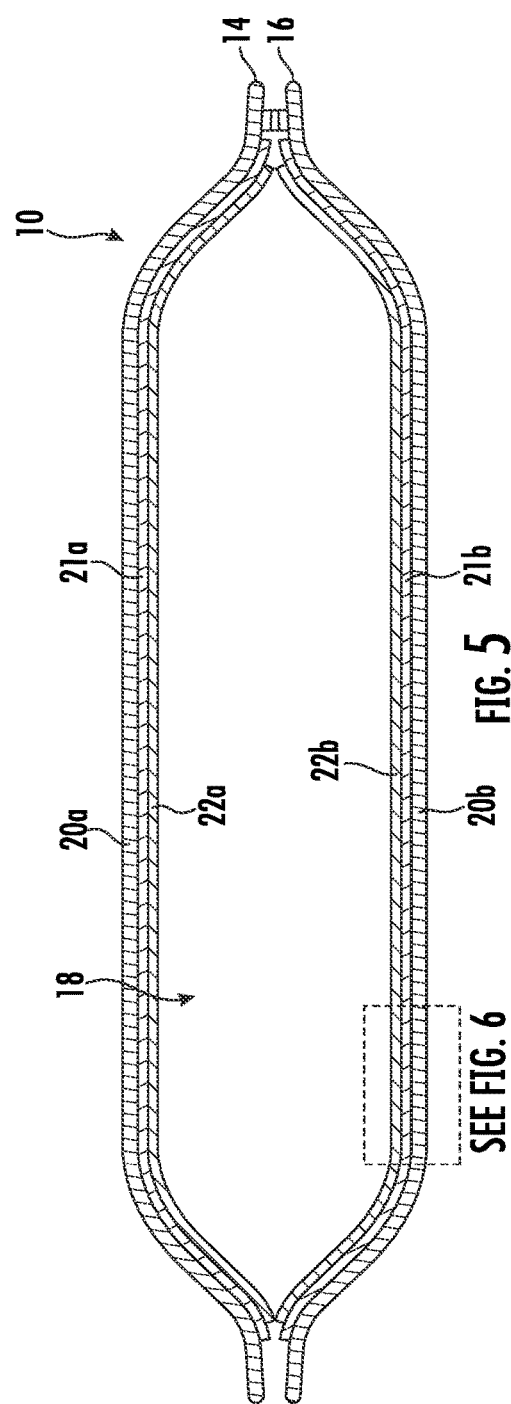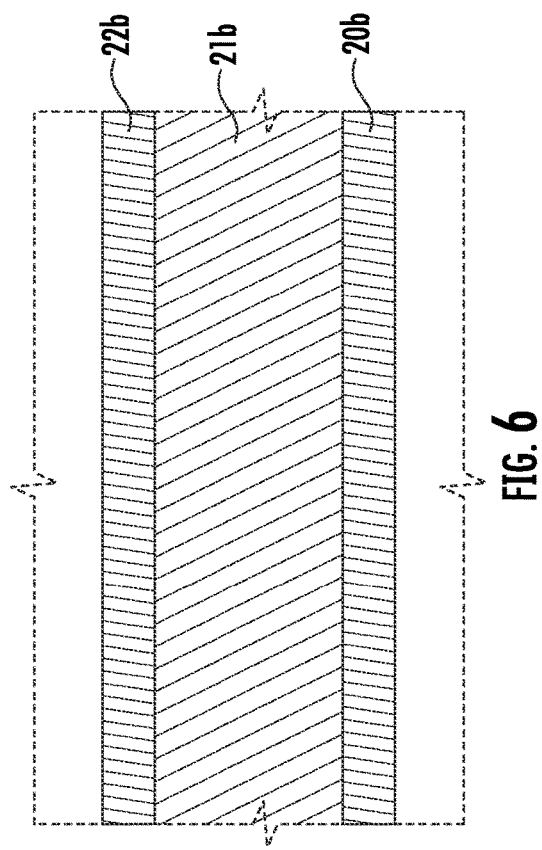

HYPOTHERMIC TREATMENT SACK

FIELD

The present disclosure relates generally to hypothermia prevention and management apparatus, and more particularly, to a hypothermia treatment sack for use in the field having a weatherproof exterior and a heat reflective interior that includes one or more heating elements.

BACKGROUND

The single major cause of death in potentially salvageable combat casualties is hemorrhage, and the greatest opportunity for reducing mortality and morbidity of battlefield casualties involves aggressive hemorrhage control modalities. In the management of combat casualties who are hemorrhaging, hypothermia prevention and management is of critical importance. Hypothermia can lead to cardiac arrhythmias, decreased cardiac output, increased systemic vascular resistance, and most importantly, induced coagulopathy by inhibition of the clotting cascade. If hypothermia is not prevented in this casualty demographic the potential exists that the injured person will not be able to form a clot due to the disruption of the clotting cascade and may potentially bleed to death from an otherwise survivable wounding.

When dealing with the rigors of combat and the treatment and prevention of hypothermia in wounded patients, known devices do not provide a sufficient solution to the unique problems encountered by medics on the battlefield. For example, the current practice by medics on the battlefield treating a patient with hypothermia is to first wrap the patient is a blanket containing air activated heating elements. These blankets are not heat reflective or weatherproof and are susceptible to rips and tears, and thus have been difficult to use in the field due to their fragility. Next, the medic will wrap the patient in a weatherproof heat reflective blanket, typically one made of lightweight aluminized polyester commonly referred to as a space blanket, around the first heating blanket to reflect the patient's body heat and heat from the blanket back against the patient. Finally, the medical will apply a heat reflective cap to the patient's head. The individual application of each of these items takes an unnecessarily long time. Worse, however, is the fact that by wrapping the patient in the heat reflective blanket, the air activated heating blanket does not get a sufficient supply of oxygen to sustain an acceptable level of heating capacity for extended time periods. Additionally, once the patient is wrapped in the blankets, the medic cannot easily check on the patient's wounds without unwrapping the patient, which exposes the patient and reduces the heat buildup around the patent intended to manage or prevent hypothermia.

Further, once the patient is wrapped in the blankets, accessing the patient to assess and address various wounds may be difficult or impossible without entirely exposing the patient to the environment.

Accordingly, an improved apparatus for hypothermia prevention is desired in the art. Particularly, an apparatus for hypothermia prevention, that allows for various body parts of the patient to be assessed without overly exposing the patient to the environment, is desired and would be appreciated in the art.

BRIEF DESCRIPTION

Aspects and advantages of the hypothermic treatment sacks in accordance with the present disclosure will be set forth in part in the following description, or may be obvious from the description, or may be learned through practice of the technology.

In accordance with one embodiment, a hypothermic treatment sack is provided. The hypothermic treatment sack includes a top sheet that defines a first outer perimeter. The hypothermic treatment sack further includes a bottom sheet that defines a second outer perimeter. The first outer perimeter of the top sheet is removably coupled to the second outer perimeter of the bottom sheet such that a patient receiving cavity is defined between the top sheet and the bottom sheet. The top sheet and the bottom sheet include a weather resistant external layer, a heat reflective interior layer, and an insulation layer. The insulation layer is disposed between the external layer and the heat reflective interior layer.

In accordance with another embodiment, a hypothermic treatment sack is provided. The hypothermic treatment sack includes a top sheet that defines a first outer perimeter. The hypothermic treatment sack further includes a bottom sheet that defines a second outer perimeter. The first outer perimeter of the top sheet is removably coupled to the second outer perimeter of the bottom sheet such that a patient receiving cavity is defined between the top sheet and the bottom sheet. The hypothermic treatment sack further includes one or more access areas that provide for selective access to the receiving cavity. The top sheet and the bottom sheet include a weather resistant external layer, a heat reflective interior layer, and an insulation layer. The insulation layer is disposed between the external layer and the heat reflective interior layer.

These and other features, aspects and advantages of the present hypothermic treatment sacks will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present hypothermic treatment sacks, including the best mode of making and using the present systems and methods, directed to one of ordinary skill in the art, is set forth in the specification, which makes reference to the appended figures, in which:

FIG. 5 is a cross-sectional view of the hypothermic treatment sack shown in FIG. 4 from along the line 5-5 in accordance with embodiments of the present disclosure; and FIG. 6 is an enlarged view of the detail shown in FIG. 5 in accordance with embodiments of the present disclosure.

DETAILED DESCRIPTION

Figure 1:
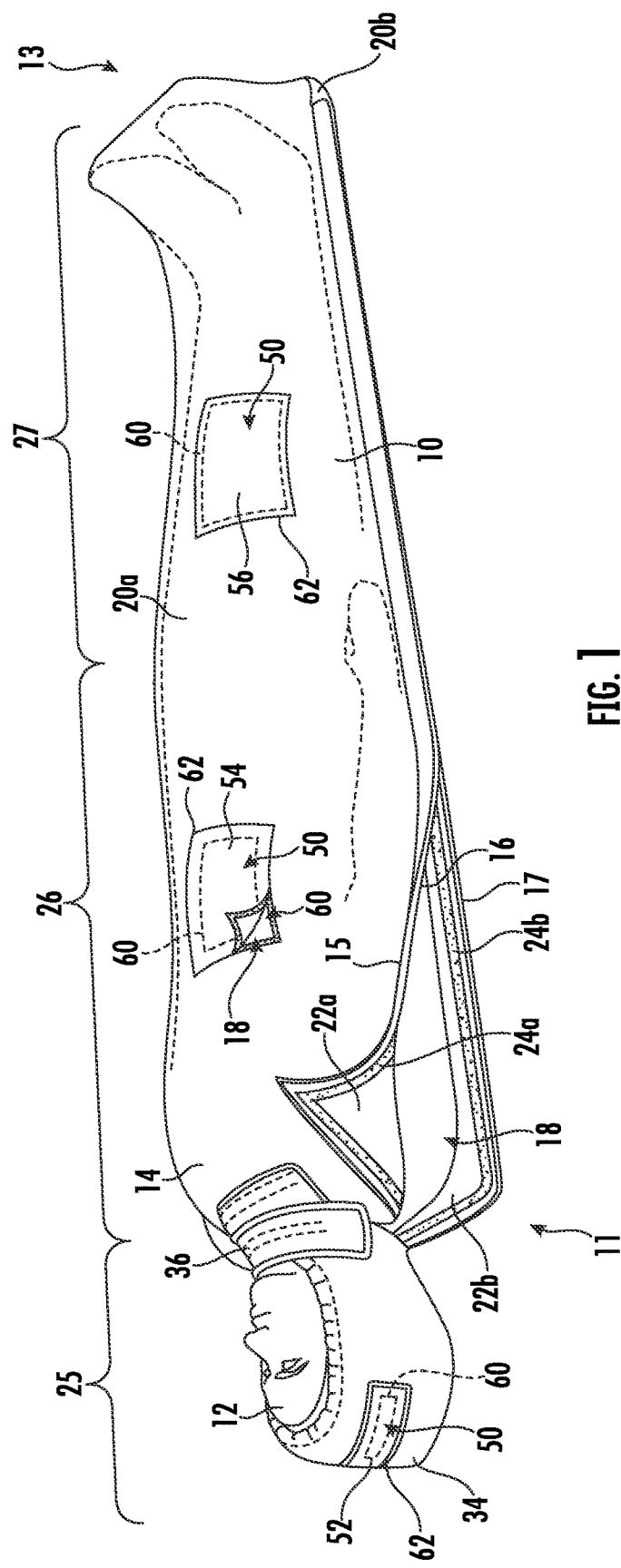
FIG. 1 is a perspective view of a hypothermic treatment sack in accordance with embodiments of the present disclosure.

Reference now will be made in detail to embodiments of the present hypothermic treatment sacks, one or more examples of which are illustrated in the drawings. Each example is provided by way of explanation, rather than limitation of, the technology. In fact, it will be apparent to those skilled in the art that modifications and variations can be made in the present technology without departing from the scope or spirit of the claimed technology. For instance, features illustrated or described as part of one embodiment can be used with another embodiment to yield a still further embodiment. Thus, it is intended that the present disclosure covers such modifications and variations as come within the scope of the appended claims and their equivalents.

The word "exemplary" is used herein to mean "serving as an example, instance, or illustration." Any implementation described herein as "exemplary" is not necessarily to be construed as preferred or advantageous over other implementations. Additionally, unless specifically identified otherwise, all embodiments described herein should be considered exemplary.

The detailed description uses numerical and letter designations to refer to features in the drawings. Like or similar designations in the drawings and description have been used to refer to like or similar parts of the invention. As used herein, the terms "first", "second", and "third" may be used interchangeably to distinguish one component from another and are not intended to signify location or importance of the individual components.

Terms of approximation, such as "about," "approximately," "generally," and "substantially," are not to be limited to the precise value specified. In at least some instances, the approximating language may correspond to the precision of an instrument for measuring the value, or the precision of the methods or machines for constructing or manufacturing the components or systems. In at least some instances, the approximating language may correspond to the precision of an instrument for measuring the value, or the precision of the methods or machines for constructing or manufacturing the components and/or systems. For example, the approximating language may refer to being within a 1, 2, 4, 5, 10, 15, or 20 percent margin in either individual values, range(s) of values and/or endpoints defining range(s) of values. When used in the context of an angle or direction, such terms include within ten degrees greater or less than the stated angle or direction. For example, "generally vertical" includes directions within ten degrees of vertical in any direction, e.g., clockwise or counter-clockwise.

The terms "coupled," "fixed," "attached to," and the like refer to both direct coupling, fixing, or attaching, as well as indirect coupling, fixing, or attaching through one or more intermediate components or features, unless otherwise specified herein. As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

Figure 2:
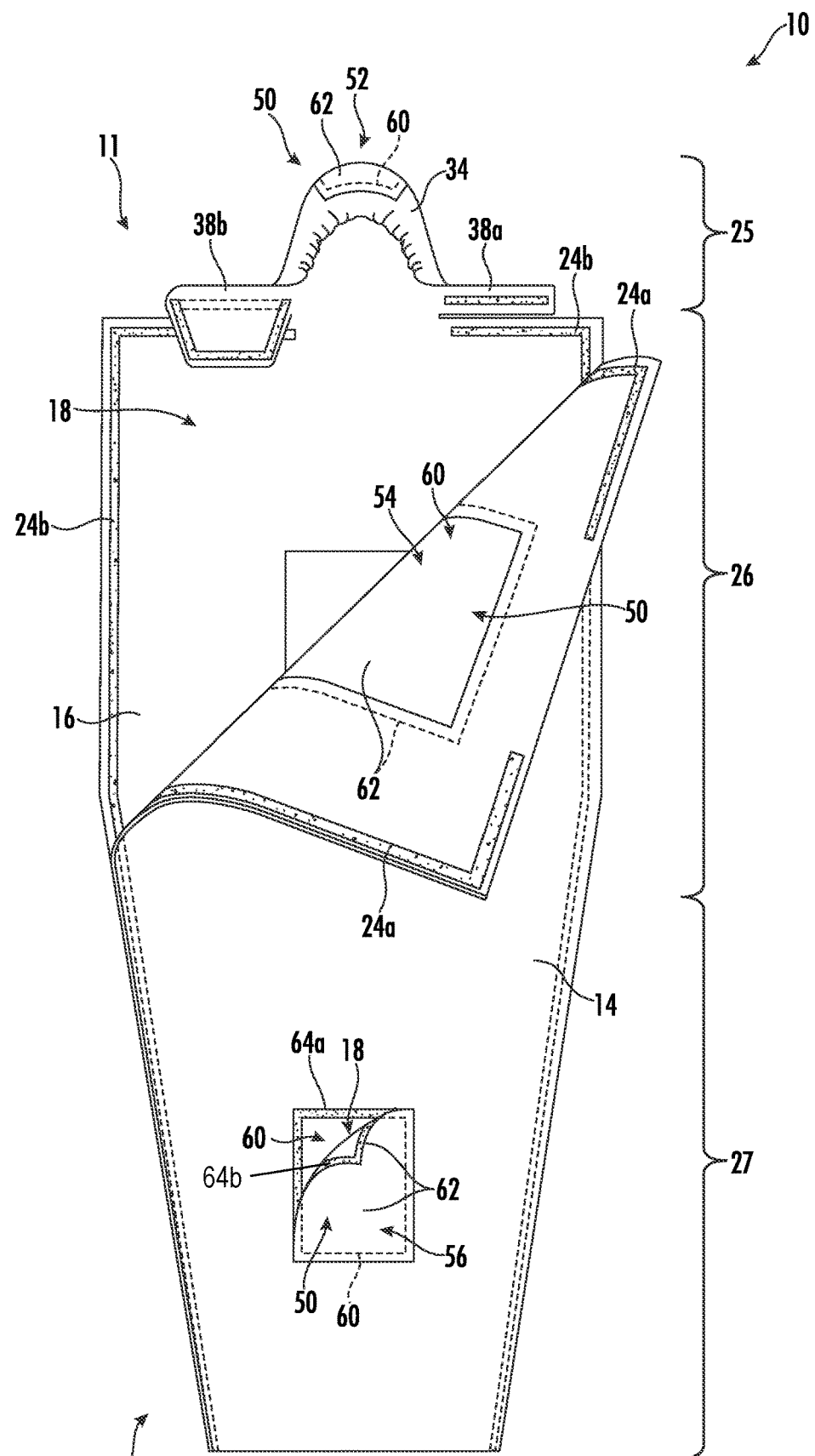
FIG. 2 is a top view of a hypothermic treatment sack in accordance with embodiments of the present disclosure.

Referring now to the drawings, FIG. 1 illustrates a perspective view of a hypothermia treatment sack 10 is shown surrounding a patient 12 for temporarily preventing and managing hypothermia. FIG. 2 illustrates a top down view of the hypothermia treatment sack 10 without the patient 12, in which hypothermia treatment sack 10 is open to show an interior. The hypothermia treatment sack 10 may be a durable cost efficient first aid device designed particularly for single use applications in the field by first responders to treat conditions associated with hypothermia by warming the patient 12 and protecting the patient 12 from inclement weather conditions until the patient 12 can be transported to the appropriate treatment facility.

The hypothermia treatment sack 10 may extend from a first end 11 to a second end 13. The hypothermia treatment sack 10 may include a top sheet 14 and a bottom sheet 16 which can have corresponding shapes so that when the bottom sheet and top sheet are engaged, a receiving cavity 18 is formed therebetween. For example, both the top sheet 14 and the bottom sheet 16 may be generally rectangularly shaped and coupled to one another along their respective perimeters to define the receiving cavity 18. Particularly, the top sheet 14 may define a first outer perimeter 15, and the bottom sheet 16 may define a second outer perimeter 17. The first outer perimeter 15 of the top sheet 14 may be removably coupled to the second outer perimeter 17 of the bottom sheet 16, such that the receiving cavity 18 is defined between the top sheet 14 and the bottom sheet 16.

The top sheet 14 and bottom sheet 16 each have a weather resistant exterior layer 20a, 20b, respectively. The weather resistant exterior layer 20a, 20b may advantageously repel wind and water from entering patient receiving cavity 18. For example, the weather resistant exterior layer 20a, 20b may form the outermost layer of the hypothermia treatment sack 10, such that the weather resistant exterior layer is directly exposed to the ambient environment. In particular embodiments, the weather resistant exterior layer 20a, 20b may be formed of a plastic material, such as polyester or polyethylene. Particularly, the weather resistant exterior layer 20a, 20b may be a woven canvas of plastic.

Further, top sheet 14 and bottom sheet 16 each have a heat reflective interior layer 22a, 22b, respectively. The heat reflective interior layer 22a, 22b, may advantageously prevent heat from escaping patient receiving cavity 18. In one embodiment, top sheet 14 and bottom sheet 16 are formed of aluminized polyester which is capable of both repelling wind and water and reflecting heat. In this arrangement, only one sheet of materials is required to form each of top sheet 14 and bottom sheet 16, which reduces bulk and weight for storage and transport in the field. Further, aluminized polyester is extremely durable and well suited to the rigors of extreme field conditions, such on a battlefield.

When top sheet 14 and bottom sheet 16 are engaged to form patient receiving cavity 18, releasable connectors 24a and 24b may be carried along a perimeter portion of top sheet 14 and bottom sheet 16 for releasably connecting or coupling the top and bottom sheets 14, 16. Particularly, releasable connector 24a may extend along the first outer perimeter 15 of the top sheet 14, and the releasable connector 24b may extend along the second outer perimeter 17 of the bottom sheet 16. This provides patient access from any location around the perimeter of the sheets when connected together. In exemplary embodiments, releasable connectors 24a and 24b may be cooperating hook and loop fasteners, such as Velcro®. However, in other embodiments, the releasable connectors 24*a* and 24*b* may be a hookless fastener or zip fastener. In some embodiments, the releasable connectors 24*a* and 24*b* may extend entirely around the respective outer perimeters 15, 17, such that the top sheet 14 may be entirely decoupled from the bottom sheet 16. In other embodiments, the releasable connectors 24*a* and 24*b* may extend only partially around the respective outer perimeters 15, 17. In such embodiments, the first outer perimeter 15 of the top sheet 14 may be non-removably coupled to the second outer perimeter 17 of the bottom sheet 16 in one or more sections. For example, in exemplary embodiments, the top sheet 14 may be non-removably coupled (such as via stitching) to the bottom sheet 16 the second end 13 of the hypothermia treatment sack 10. Alternatively, the hypothermia treatment sack 10 may be constructed from a singular sheet folded on itself to define the receiving cavity 18. For example, in such embodiments, the single sheet may be folded at the second end 13 and may have a top portion (e.g., the top sheet 14) and a bottom portion (e.g., the bottom sheet 16).

In many embodiments, a hood 34 may extend from the first end 11 of the hypothermia treatment sack 10. The hood 34 may be an extension of the bottom sheet 16, such that the hood 34 is formed from the same materials as the bottom sheet 16. Alternatively, the hood 34 may be formed from different materials and/or may be coupled to the bottom sheet 16 (e.g., stitched). For example, the hood 34 may extend from and be carried by bottom sheet 16. The hood 34 may advantageously cover a patient's head when placed in the receiving cavity 18. In a further embodiment, hood 34 includes a weather resistant exterior layer for repelling wind and water from a patient's head. Further, hood 34 can include a heat reflective internal layer for preventing heat from escaping through the hood. As with top sheet 14 and bottom sheet 16, hood 34 may be constructed from aluminized polyester to provide lightweight durable wind and water resistance while also providing heat reflective capability.

In some embodiments, a neck closure 36, is carried by hood 34 and adapted for surrounding a patient's neck. Preferably, the neck closure 36 includes a weatherproof exterior side for repelling wind and water from the patient's neck, and a heat reflective interior liner for reducing heat loss from the patient's neck. Neck closure 36 can include a first flap 38*a* including a first portion of hook and loop fastener, and a second flap 38*b* including a second portion of cooperating hook and loop fastener for engaging hook and loop fastener of first flap, wherein first flap 38*a* and second flap overlap 38*b* each other around a patient's neck.

In various embodiments, the hypothermia treatment sack 10 may include a head area 25, a torso area 26, and a leg area 27. For example, the head area 25 may be the area in which a patient's head is held during use of the hypothermia treatment sack 10 (e.g., the hood 34). For example, the head area 25 may extend from a top of the hood 34 to a first end 11 of the hypothermia treatment sack 10. The torso area 26 may be the area in which a patient's torso is held during use of the hypothermia treatment sack 10. For example, the torso area 26 may extend from the first end 11 to the leg area 27. Further, the leg area 27 may be the area in which a patient's legs are held during use of the hypothermia treatment sack 10. For example, the leg area 27 may extend from the torso area 26 to the second end 13.

In many implementations, as shown in FIG. 2, one or more heating elements 66 may be disposed in the receiving cavity 18 for warming the patient 12. For example, the one or more heating elements 66 may be one or more self-activating heating pads for producing heat when exposed to air. The self-activating heating pads may include various combinations of iron powder, water, salt, and activated carbon which produces an exothermal reaction when exposed to oxygen.

In many embodiments, the hypothermia treatment sack 10 may include one or more access areas 50 that provide for selective access to the receiving cavity 18. For example, each of the access areas 50 may be a flap or otherwise temporarily removable portion of the top sheet 14 or bottom sheet 16 that provides for selective access to the receiving cavity 18 without overly exposing the patient 12 disposed therein to the ambient environment. The one or more access areas 50 may advantageously allow one or more wounds or injuries of the patient 12 to be addressed without overly exposing the patient 12 to the potentially harsh ambient environment. Additionally, the one or more access areas 50 may allow for the heating element 66 to be moved as necessary without having to open the entire hypothermia treatment sack 10. In exemplary embodiments, the one or more access areas 50 may include one or more head access areas 52 disposed in the head area 25 (e.g., on the hood 34), one or more chest access areas 54 disposed in the torso area 26 (e.g., in the top sheet 14 and/or the bottom sheet 16), and one or more leg access areas 56 disposed in the leg area 27.

As shown in FIG. 2, each of the access areas 50 may include an opening 60 that is defined in the hypothermia treatment sack 10 (e.g., in one of the top sheet 14 and/or the bottom sheet 16). The opening 60 may be a cut-out or through-hole defined in the top or bottom sheet 14, 16 to provide access to the receiving cavity without requiring the top sheet 14 to be decoupled from the bottom sheet 16. The opening 60 may be a variety of shapes (e.g., depending on location on the hypothermia treatment sack 10), such as rectangular, circular, polygonal, or other shapes.

Additionally, each of the access areas 50 may include a cover sheet 62 that extends across the opening 60. For example, the cover sheet 62 may be removably coupled to the top or bottom sheet 14, 16 and may extend across the opening 60, such that the cover sheet 62 may be selectively removed (either entirely or partially) to provide access to the receiving cavity 18. In some embodiments, the cover sheet 62 may have a slightly larger (e.g., between about 1% and about 10%) surface area than the opening 60, such that the cover sheet 62 may extend entirely across the opening 60 without any gaps or voids. This may advantageously allow the receiving cavity 18 to maintain maximum thermal insulation when the access area 50 is not being used.

In exemplary embodiments, as shown in FIG. 2, releasable connectors 64*a* and 64*b* may extend along a perimeter portion of the opening 60 and the cover sheet 62 respectively for releasably connecting the cover sheet 62 to one of the top or bottom sheets 14, 16. In exemplary embodiments, releasable connectors 64*a* and 64*b* may be cooperating hook and loop fasteners, such as Velcro®. However, in other embodiments, the releasable connectors 64*a* and 64*b* may be a hookless fastener or zip fastener (such as a zipper).

Figure 3:
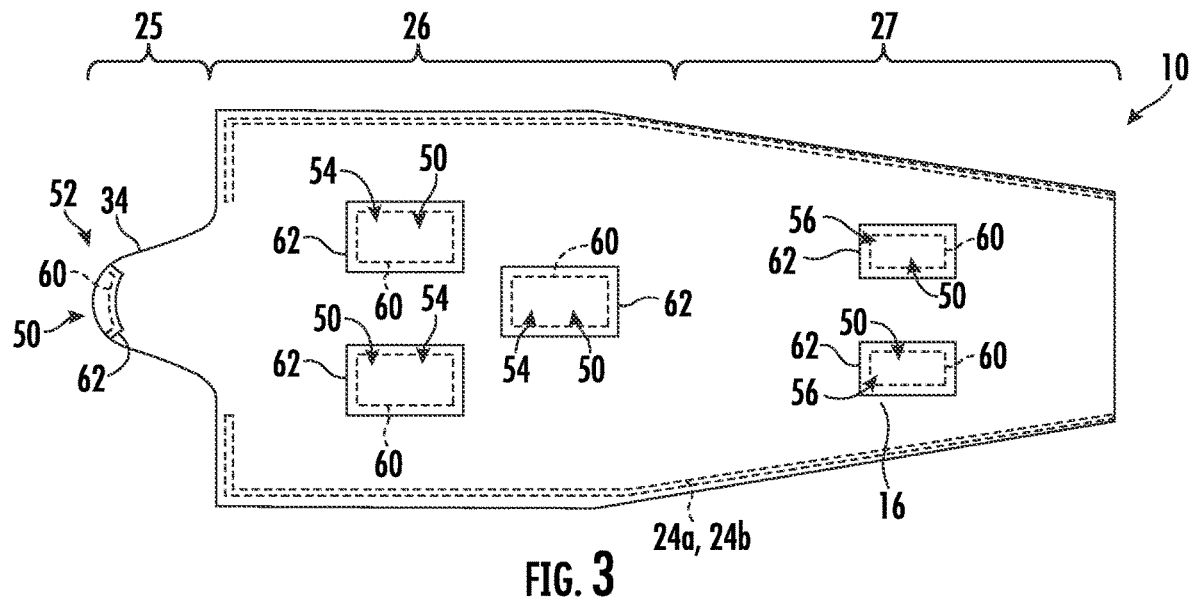
FIG. 3 is a bottom view of a hypothermic treatment sack in accordance with embodiments of the present disclosure.
Figure 4:
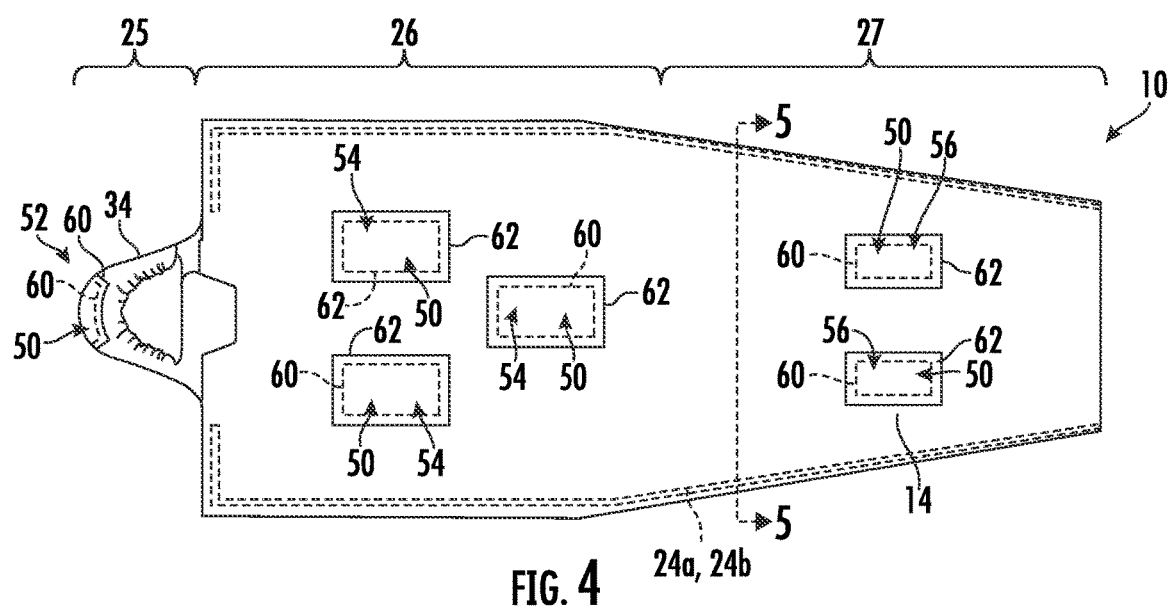
FIG. 4 is a top view of a hypothermic treatment sack in accordance with embodiments of the present disclosure.

FIG. 3 illustrates a bottom view of the hypothermia treatment sack 10 (e.g., a view of the bottom sheet 16), and FIG. 4 illustrates a top view of the hypothermia treatment sack 10, in accordance with embodiments of the present disclosure. As shown, in exemplary embodiments, the one or more access areas 50 may be disposed on one or both of the top sheet 14 and/or the bottom sheet 16. This may advantageously allow for the receiving cavity 18 to be accessed from both the top and the bottom of the hypothermia treatment sack 10. For example, for access areas 50 disposed on the top sheet 14 (FIG. 4), the opening 60 may be defined in the top sheet 14, and the cover sheet 62 may extend across the opening 60 and releasably (or removably) couple to the top sheet 14 via the releasable connectors 64a, 64b (FIG. 2). Similarly, for access areas 50 disposed on the bottom sheet 16 (FIG. 3), the opening 60 may be defined in the bottom sheet 16, and the cover sheet 62 may extend across the opening 60 and releasably (or removably) couple to the bottom sheet 16 via the releasable connectors 64a, 64b (FIG. 2).

FIG. 5 illustrates a cross-sectional view of the hypothermia treatment sack 10 from along the line 5-5 shown in FIG. 4, and FIG. 6 illustrates an enlarged view of the boxed detail in FIG. 5, in accordance with embodiments of the present disclosure. As shown, each of the top sheet 14 and the bottom sheet 16 may include one or more layers of material stacked together and coupled to one another. For example, both the top sheet 14 and the bottom sheet 16 may include a weather resistant exterior layer 20a, 20b, respectively. The weather resistant exterior layer 20a, 20b may advantageously repel wind and water from entering patient receiving cavity 18. For example, the weather resistant exterior layer 20a, 20b may for the outermost layer of the hypothermia treatment sack 10, such that the weather resistant exterior layer 20a, 20b is directly exposed to the ambient environment. In particular embodiments, the weather resistant exterior layer 20a, 20b may be formed of a plastic material, such as polyester or polyethylene. Particularly, the weather resistant exterior layer 20a, 20b may be a woven canvas of plastic.

In a further advantageous embodiment, the weather resistant exterior layers 20a and 20b of top and bottom sheets 14 and 16, respectively, may be a generally dark green color, such as olive drab, for camouflaging injured patients on a battlefield. Additionally or alternatively, the weather resistant exterior layers 20a and 20b of top and bottom sheets 14 and 16, respectively, may be a camouflage pattern. In order to reduce manufacturing costs, heat reflective interior layer 22a and 22b may be the standard reflective finish common to aluminized polyester, which can be used to attract attention of rescuers if required.

Additionally, in exemplary embodiments, the top sheet 14 and the bottom sheet 16 may each include a heat reflective interior layer 22a, 22b, respectively. The heat reflective interior layer 22a, 22b, may advantageously prevent heat from escaping patient receiving cavity 18. In one embodiment, the heat reflective interior layer 22a, 22b is formed of aluminized polyester which is capable of both repelling wind and water and reflecting heat. Further, aluminized polyester is extremely durable and well suited to the rigors of extreme field conditions, such on a battlefield.

In exemplary embodiments, both the top sheet 14 and the bottom sheet 16 may include an insulation layer 21a, 21b disposed between the respective weather resistant exterior layer 20a, 20b and the respective heat reflective interior layer 22a, 22b. The insulation layer 21a, 21b may advantageously prevent heat from escaping the receiving cavity 18. As shown in FIG. 6, the insulation layer 21b (which may also be representative of the insulation layer 21a) may define a thickness that is greater than the thickness of the weather resistant exterior layer 20b and the heat reflective interior layer 22b.

In various embodiments, the insulation layer 21a, 21b may be a woven insulating fabric. For example, the insulation layer 21a, 21b may be composed of at least one of a down, a fleece, and/or a wool. For example, the down may be a plurality of compacted feathers (e.g., plumage), the fleece may be a collection of polyester fibers or filaments either mechanically held together (e.g., woven or stitched) or otherwise bound together with a bonding material (such as a polyester adhesive). The wool insulation may be made from sheep wool fibers or filaments that are either mechanically held together (e.g., woven or stitched) or bonded together (e.g., using a polyester adhesive) to form insulating batts, rolls and ropes.

In many embodiments, the insulation layer 21a, 21b may have an R-value that is particularly advantageous for use with the hypothermia treatment sack 10. As should be understood, the R-value is a measure of how well a two-dimensional barrier, such as the insulation layer 21a, 21b, resists the conductive flow of heat. R-value is the temperature difference per unit of heat flux needed to sustain one unit of heat flux between the warmer surface and colder surface of a barrier under steady-state conditions. Particularly, in some embodiments, the insulation layer 21a, 21b may have an R-value of between about 5 and about 0.5. In other embodiments, the insulation layer 21a, 21b may have an R-value of between about 4 and about 1. In various embodiments, the insulation layer 21a, 21b may have an R-value of between about 3.5 and about 1.5. In particular embodiments, the insulation layer 21a, 21b may have an R-value of about 2.

Additionally, the insulation layer 21a, 21b may be formed of a continuous filament polyester, which may provide multiple advantages over other forms of insulation (e.g., fleece or others). Fore example, the continuous filament may be lightweight, lofty, durable, thermally efficient, and resilient than other insulations. Additionally, forming the insulation layer 21a, 21b from a continuous filament of polyester may have hydrophobic properties, such that it maintains thermal efficiency when wet. Yet sill further, its resilient properties may allow the hypothermia treatment sack 10 to be tightly packaged (e.g., in a vacuum seal).

In exemplary embodiments, the insulation layer 21a, 21b may define a ratio of R-value and specific weight (e.g., weight per unit area) of between about 0.3 and about 0.7, or such as about 0.4 and about 0.6, or such as about 0.5. This ratio may advantageously allow the insulation layer to provide increased thermal efficiency without adding large amounts of weight, which would otherwise make the hypothermia treatment sack difficult to package and carry. For example, in many embodiments, the insulation layer 21a, 21b may include a specific weight (e.g., weight per unit area) of between about 0.5 oz per square yard and about 10 oz per square yard. In other embodiments, the insulation layer 21a, 21b may include a specific weight (e.g., weight per unit area) of between about 1 oz per square yard and about 8 oz per square yard. In some embodiments, the insulation layer 21a, 21b may include a specific weight (e.g., weight per unit area) of between about 2 oz per square yard and about 6 oz per square yard. In certain embodiments, the insulation layer 21a, 21b may include a specific weight (e.g., weight per unit area) of between about 3 oz per square yard and about 4 oz per square yard.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A hypothermia treatment sack comprising:
a top sheet defining a first outer perimeter; and
a bottom sheet defining a second outer perimeter, the first outer perimeter of the top sheet removably coupled to the second outer perimeter of the bottom sheet such that a patient receiving cavity is defined between the top sheet and the bottom sheet, wherein the top sheet and the bottom sheet comprise:
a weather resistant external layer provided as an outermost layer to prevent wind and water from passing through the outermost layer;
a heat reflective interior layer comprising aluminized polyester; and
an insulation layer enclosed between the weather resistant external layer and the heat reflective interior layer, wherein the insulation layer is formed of a continuous filament polyester that is hydrophobic, and wherein the insulation layer defines a ratio of R-value and specific weight of between about 0.3 and about 0.7.

2. The hypothermia treatment sack as in claim 1, wherein the insulation layer is a woven insulating fabric.

3. The hypothermia treatment sack as in claim 1, further comprising one or more access areas that provide for selective access to the patient receiving cavity.

4. The hypothermia treatment sack as in claim 3, wherein the one or more access areas are disposed on one of the top sheet and the bottom sheet.

5. The hypothermia treatment sack as in claim 3, wherein the one or more access areas comprises:
an opening defined in one of the top sheet or the bottom sheet, the opening providing access to the patient receiving cavity; and
a cover sheet extending across the opening and removably coupled to the one of the top sheet or the bottom sheet.

6. The hypothermia treatment sack as in claim 5, wherein one or more releasable connectors couple the cover sheet to one of the top sheet or the bottom sheet.

7. The hypothermia treatment sack as in claim 5, wherein a releasable connector extends along a perimeter of the opening and the cover sheet for releasably connecting the cover sheet to one of the top sheet or the bottom sheet.

8. The hypothermia treatment sack as in claim 5, wherein the cover sheet has a first surface area that is larger than a second surface area of the opening.

9. The hypothermia treatment sack as in claim 3, wherein the hypothermia treatment sack defines a head area, a torso area, and a leg area.

10. The hypothermia treatment sack as in claim 9, wherein the one or more access areas is defined in each of the head area, the torso area, and the leg area.

11. The hypothermia treatment sack as in claim 1, further comprising one or more heating elements disposed within the receiving cavity.

12. The hypothermia treatment sack as in claim 1, wherein the bottom sheet further comprises a hood extending from the bottom sheet, the hood including a neck closure formed from a first flap and a second flap.

13. A hypothermia treatment sack comprising:
a top sheet defining a first outer perimeter;
a bottom sheet defining a second outer perimeter, the first outer perimeter of the top sheet removably coupled to the second outer perimeter of the bottom sheet such that a patient receiving cavity is defined between the top sheet and the bottom sheet; and
one or more access areas that provide for selective access to the patient receiving cavity, wherein the top sheet and the bottom sheet comprise:
a weather resistant external layer provided as an outermost layer to prevent wind and water from passing through the outermost layer;
a heat reflective interior layer comprising aluminized polyester; and
an insulation layer enclosed between the weather resistant external layer and the heat reflective interior layer, wherein the insulation layer is formed of a continuous filament polyester that is hydrophobic, and wherein the insulation layer defines a ratio of R-value and specific weight of between about 0.3 and about 0.7.

14. The hypothermia treatment sack as in claim 13, wherein the insulation layer is a woven insulating fabric.

15. The hypothermia treatment sack as in claim 13, wherein the one or more access areas are disposed on one of the top sheet and the bottom sheet.

16. The hypothermia treatment sack as in claim 13, wherein the one or more access areas comprises:
an opening defined in one of the top sheet or the bottom sheet, the opening providing access to the patient receiving cavity; and
a cover sheet extending across the opening and removably coupled to the one of the top sheet or the bottom sheet.

17. The hypothermia treatment sack as in claim 16, wherein one or more releasable connectors couple the cover sheet to one of the top sheet or the bottom sheet.

18. The hypothermia treatment sack as in claim 13, wherein the hypothermia treatment sack defines a head area, a torso area, and a leg area.

19. The hypothermia treatment sack as in claim 18, wherein the one or more access areas is defined in at least one of the head area, the torso area, and the leg area.

20. The hypothermia treatment sack as in claim 13, further comprising one or more heating elements disposed within the patient receiving cavity.

* * * * *